United States Patent
Calasso

(10) Patent No.: US 9,935,688 B2
(45) Date of Patent: Apr. 3, 2018

(54) SYSTEM FOR MEDICAL TREATMENT

(71) Applicant: Irio Giuseppe Calasso, Arth (CH)

(72) Inventor: Irio Giuseppe Calasso, Arth (CH)

(73) Assignee: MEDIRIO S.A., Visp (CH)

( * ) Notice: Subject to any disclaimer, the term of this patent is extended or adjusted under 35 U.S.C. 154(b) by 741 days.

(21) Appl. No.: 13/740,427

(22) Filed: Jan. 14, 2013

(65) Prior Publication Data
US 2013/0181538 A1 Jul. 18, 2013

(30) Foreign Application Priority Data

Jan. 17, 2012 (EP) .................................. 12151476

(51) Int. Cl.
*H04B 5/00* (2006.01)
*A61M 5/14* (2006.01)
*A61M 5/142* (2006.01)

(52) U.S. Cl.
CPC ......... *H04B 5/0037* (2013.01); *A61M 5/1413* (2013.01); *A61M 5/14248* (2013.01); *A61M 5/14276* (2013.01); *A61M 2005/14268* (2013.01); *A61M 2205/3515* (2013.01); *A61M 2205/3523* (2013.01); *A61M 2205/3569* (2013.01); *A61M 2205/3592* (2013.01); *A61M 2205/60* (2013.01); *A61M 2205/6054* (2013.01); *A61M 2205/8287* (2013.01)

(58) Field of Classification Search
CPC ............ H02J 17/00; A61M 2205/8243; A61M 2205/8287
USPC ........................................... 307/104; 320/108
See application file for complete search history.

(56) References Cited

U.S. PATENT DOCUMENTS

| | | | | |
|---|---|---|---|---|
| 4,041,954 A | * | 8/1977 | Ohara | .................. A61N 1/3787 128/908 |
| 5,314,453 A | * | 5/1994 | Jeutter | .................. A61N 1/3787 607/60 |
| 6,740,059 B2 | | 5/2004 | Flaherty | |

(Continued)

FOREIGN PATENT DOCUMENTS

| | | |
|---|---|---|
| WO | WO 02/068015 A2 | 9/2002 |
| WO | 2005018708 A2 | 3/2005 |

(Continued)

*Primary Examiner* — Fritz M Fleming
(74) *Attorney, Agent, or Firm* — Robert E. Alderson Jr.

(57) ABSTRACT

The present invention refers to a system for medical treatment comprising a medical device and a separate hand-held device. The medical device comprises an energy-receiving unit and the separate hand-held device comprises a housing and an energy-transfer unit to transfer energy to be used at least in part for performing medical treatment to the energy-receiving unit of the medical device when the energy-receiving unit and the energy-receiving unit are in an energy-transfer position. The system further comprises at least one position sensor adapted to detect at least when the energy-transfer unit and the energy-receiving unit are in the energy-transfer position. The system further comprises a controller for controlling the energy-transfer unit such that the transfer of energy needed for medical treatment from the energy-transfer unit to the energy-receiving unit is enabled only when the energy-transfer unit and the energy-receiving unit are in the energy-transfer position.

14 Claims, 4 Drawing Sheets

(56) References Cited

U.S. PATENT DOCUMENTS

| | | | | |
|---|---|---|---|---|
| 2006/0232408 A1* | 10/2006 | Nycz | .................... | G06F 19/323 340/572.1 |
| 2010/0217353 A1* | 8/2010 | Forsell | .................... | H02J 5/005 607/61 |
| 2010/0292759 A1* | 11/2010 | Hahn | .................... | A61N 1/375 607/57 |
| 2010/0305663 A1* | 12/2010 | Aghassian | ........... | A61N 1/3605 607/61 |

FOREIGN PATENT DOCUMENTS

| | | | |
|---|---|---|---|
| WO | | 2009019648 A | 2/2009 |
| WO | WO | 2009/016635 A2 | 2/2009 |
| WO | WO | 2009/144726 | 12/2009 |
| WO | | 2010072010 A2 | 7/2010 |
| WO | WO | 2010/072005 | 7/2010 |

* cited by examiner

SYSTEM FOR MEDICAL TREATMENT

FIELD OF THE INVENTION

The present invention relates to a system for medical treatment comprising a medical device to be placed in contact with a patient and a separate hand-held device, the medical device comprising an energy-receiving unit and the hand-held device comprising an energy-transfer unit to transfer energy to the energy-receiving unit of the medical device, when the energy-receiving unit and the energy-receiving unit are in an energy-transfer position. The present invention also refers to a method of controlling the medical device by the hand-held device.

BACKGROUND OF THE INVENTION

Many medical conditions often require medical treatment such as the regular administration of doses of medicaments. These medicaments are often provided as liquid solutions to be administered intravenously or trans-dermally. Diabetic patients, for example, may require several injections of insulin every day. Patients with chronic diseases may require frequent doses of a pain drug, etc. . . . Mostly, injection pen devices are used by these patients, because they allow an easier and more convenient administration of doses of medicament than with standard syringe and vial. Pen devices however require complex manipulations too, e.g. assembling a new needle every time, replacing a medicament vial when empty, and force the patient to make a new injection every time. This may cause various problems like possible contamination, uncomfortable and embarrassing situation in public place, sore body parts due to multiple injection points. In the attempt to make the life of these patients easier, infusion devices have been developed. The infusion devices known in the art typically comprise a storage device, such as a cartridge, a syringe, a reservoir, containing the liquid medicament, and use electro-mechanical pumping to deliver the medicament to the patient via tubing to a needle that is inserted through the skin. They typically comprise also all the elements needed for operation and control, e.g. a processor, electric components, a battery, buttons or switches located on the housing of the device, visual feedback via text or graphic screens, such as LCDs, etc. . . . . Such devices can be worn in a harness or pocket or strapped to the body of the patient. Currently available infusion devices are expensive, difficult to program and use and tend to be bulky and heavy. Filling these devices can be difficult and require specialized care, maintenance, and cleaning to assure proper functionality and safety for their intended long-term use. In U.S. Pat. No. 6,740,059 an infusion device is disclosed comprising an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. This infusion device is provided with a housing that is free of user input components, such as a keypad or visual screen as these features have been transferred to a separate remote device thus reducing size and complexity of the infusion device. The infusion device, however, still retains all the electro-mechanical components, such as a driving motor, a processor, a battery to provide energy to be used for the medical treatment, and since it needs to be replaced after a few days, it appears to be a very expensive disposable.

In WO 02/068015 a system for the continuous delivery of a medicament is disclosed, the system including a disposable assembly having an exit port assembly and a metering portion of a dispenser for controlling fluid flow to the exit port assembly, and a reusable assembly having a control portion of the dispenser adapted to control the metering portion of the dispenser upon attachment of the reusable assembly and the disposable assembly, a local processor connected to the dispenser and programmed to cause fluid flow to the exit port assembly through the dispenser based upon flow instructions, and a local wireless communication element connected to the local processor for receiving flow instructions from a remote wireless device. The assemblies are adapted to be removably attached, and a power source is contained in the disposable assembly for providing power for the medical treatment to the reusable assembly upon attachment of the reusable assembly and the disposable assembly. Such a system is complex, large, indiscreet and expensive and it may be unsafe. WO 2005/018708 discloses a magnetically coupled implantable actuation system utilizing a magnetically coupled drive mechanism configured to transfer energy to an implantable medical device to be used for medical treatment, in this case for regulating the flow of a fluid. One variation comprises a drive magnet having a first radius and adapted to rotate about a longitudinal axis when urged, and a driven magnet defining a second radius, which is less than the first radius. This driven magnet is adapted to be implanted within a body and rotate about the longitudinal axis when coaxially positioned within a receiving cavity defined by the drive magnet such that magnetic coupling occurs circumferentially between the driven magnet and the drive magnet. An optional anchor can be used to secure the implanted driven magnet housing against any rotational forces or moments by securing the housing within the subcutaneous layer. This system is however unsafe since it is susceptible to external interferences, such as when in the presence of strong electromagnetic fields, which may cause unwanted rotation of the driven magnet.

WO 2010072010, which is incorporated herein by reference, solves some of the problems described above, by providing a system comprising a delivery device, which is small, comprises a minimum number of components, is easily manufactured, is thus cost-effective and may be disposable. Moreover, the system is safe to use and secure against possible interferences by means of a control unit, which can be activated only in a specific manner and thus eliminates the risk that medicament treatment is carried out when not required.

SUMMARY OF THE INVENTION

It is against the above background that the present invention provides certain unobvious advantages and advancements over the prior art. In particular, the present invention provides a system for medical treatment, which is even safer and more reliable to use.

The system comprises a medical device to be placed in contact with a patient and a separate hand-held device wherein the medical device comprises an energy-receiving unit and the separate hand-held device comprises a housing and an energy-transfer unit to transfer energy to be used at least in part for performing medical treatment to the energy-receiving unit of the medical device when the energy-receiving unit and the energy-receiving unit are in an energy-transfer position. The system further comprises at least one position sensor adapted to detect at least when the energy-transfer unit and the energy-receiving unit are in the energy-transfer position. The system further comprises a controller for controlling the energy-transfer unit such that the transfer of energy needed for medical treatment from the energy-transfer unit to the energy-receiving unit is enabled only when the energy-transfer unit and the energy-receiving unit are in the energy-transfer position.

The present invention also refers to a method of controlling the medical device by the hand-held device.

In this way the system is enabled to transfer energy needed for medical treatment from the energy-transfer unit to the energy-receiving unit only when the medical device and the hand-held device are in a position, which enables transfer of the correct amount of energy needed for the medical treatment. The system may be configured such that energy is not transferred until the energy-transfer position has been reached and verified. The system may also be controlled such that the relative positioning of the energy-transfer unit and the energy-receiving unit is monitored during the transfer of energy and e.g. an alert is generated and/or the transfer of energy is interrupted if the energy-transfer unit and the energy-receiving unit are no loner in the energy-transfer position, e.g. if the energy transfer position is lost. The system may also be configured such as to guide the hand-held device towards the medical device until the energy-transfer position is reached. The system may also be configured such that the positioning of the energy-transfer unit is automatically adjusted with respect to the housing of the hand-held device such as to facilitate the achievement of the energy-transfer position. One advantage of the present invention is that the system can be used with safety regardless of the shape of the medical device and the hand-held device, e.g. it is no longer important to have a hand-held device, which is complementary in shape to the medical device such as to obtain alignment between the energy-transfer unit and the energy-receiving unit. The system of the present invention is particularly useful when alignment or correct positioning is difficult to verify, e.g. when one or more layers of clothes are between the medical device and the hand-held device or when the medical device is implanted. In such cases, without the system of the present invention, energy may be sent by the energy-transfer unit but not received or received only in part by the energy-receiving unit without the system knowing or knowing only after energy has been sent if energy has been used, typically without being able to quantify how much of the energy has been actually used for medical treatment. With the system of the present invention it is assured that energy is sent only when it can be received and used for medical treatment. Another advantage is that, given the higher degree of safety, the system of the present invention may be designed such as to require less energy, e.g. in the range of energy amounts from otherwise interfering naturally or artificially energy-sources, which are likely to occur in the environment. It is therefore possible to design the energy-transfer unit and the energy-receiving unit with lower requirements on mechanical strength, with less and/or smaller and/or weaker (involving smaller forces) energy-transfer and/or energy-receiving elements, thereby gaining reduction in size, reduction in complexity and reduction in costs.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

DETAILED DESCRIPTION OF THE INVENTION

Figure 1:
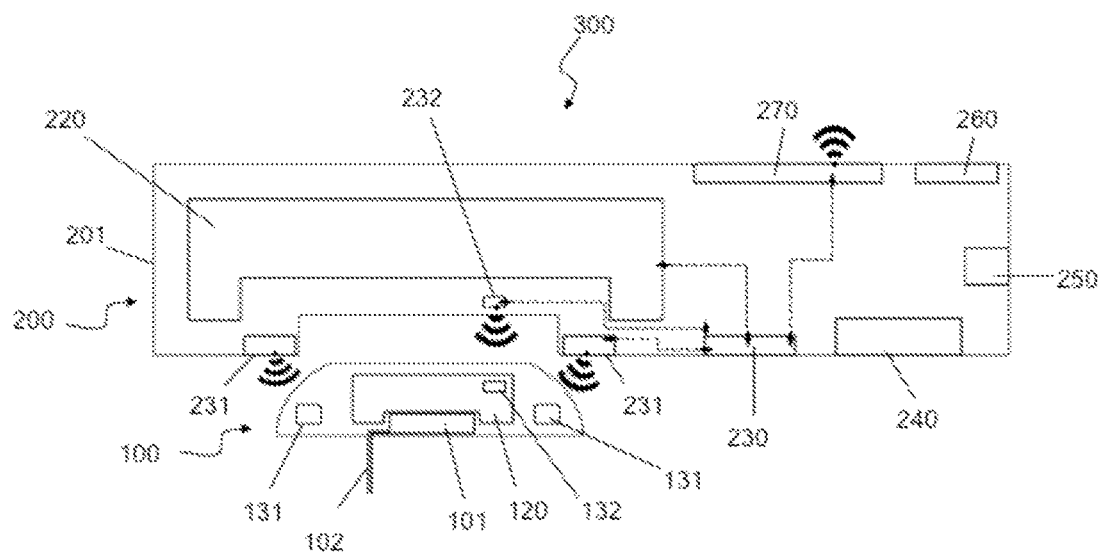
FIG. 1 depicts schematically a system for medical treatment comprising a medical device and a separate hand-held device in the energy-transfer position.

The system of the present invention comprises a medical device to be placed in contact with a patient. A "medical device" according to the present invention is a device, which is adapted to perform medical treatment when placed in contact with a patient and when receiving energy externally from a hand-held device by temporarily placing the hand-held device in an energy-transfer position when medical treatment is required. "In contact" means either in dermal contact with the user, e.g. removably fixed, e.g. by means of an adhesive base, to the skin of the patient, or more generally in body contact, comprising the inside of the body, such as fixed at least in part in a cavity of the body or implanted in the body. According to one embodiment the medical device is a medical delivery device adapted to deliver trans-dermally or intravenously multiple discrete doses of a medicament to a patient without the need of multiple injections. A typical example of patient is a diabetic patient requiring frequent doses of insulin, e.g. in correspondence of each meal. According to one embodiment medical treatment thus means treatment of a metabolic disorder, such as a disorder of the glucose metabolism. According to one embodiment the medical device is an implanted device or a device partly in the body and partly out of the body, e.g. a catheter, adapted for regulating the flow of a fluid. The medical device may be thus embodied as a valve device adapted to enable/disable fluid flow or vary the flow rate of a fluid, e.g. a body fluid, or as a continuous delivery device, adapted to deliver a continuous flow of a medicament with a variable flow rate over a prolonged period of time. Medical treatment may therefore result from regulation of the flow of a fluid from outside the body into the body or from inside the body to the external of the body, e.g. to drain off excess of a fluid produced by the body, e.g. due to a pathological condition, or from regulation of the flow of a body fluid within the body, i.e. from one part of the body to another.

According to one embodiment the medical device comprises a reservoir for holding a volume of a medicament to be delivered which is sufficient for several doses. Typically, the medical device is replaced after a period of time, e.g. 1 to 7 days, typically 2 to 4 days, after several doses of the medicament have been delivered, e.g. when the medicament is exhausted. In case of an implanted medical device, the medical device may be adapted to be replaced after a longer period of time. The reservoir may be of any type, e.g. a syringe or syringe-like, a collapsible pouch, a coiled tube, and may be either pre-loaded with the medicament or adapted to be loaded by the user just before use.

According to one embodiment the reservoir for holding the medicament to be delivered is a syringe type reservoir comprising a first end and at least one opening in correspondence of said first end for pumping medicament to the trans-dermal injection element and/or for introducing the medicament in the syringe, a second end, and walls between said first end and said second end into which a first axial pump element fits in a fluid tight manner. A syringe may be intended also as a tube of any length and shape.

According to one embodiment the medical device comprises a re-usable component adapted to be joinable to a disposable component, wherein the disposable component comprises the reservoir for holding the medicament and the re-usable component comprises the energy-receiving unit, and wherein the disposable component is configured to be replaced after a period of time or when the medicament is exhausted, and the re-usable component is adapted to be re-used with a new disposable component.

According to one embodiment the medical device comprises at least one injection element, which is adapted to penetrate at least partially the skin or a blood vessel of the patient and remain in a trans-dermal or intravenous position for the duration of use of the medical device. The injection element may be a thin needle, inserted at a controlled depth, a cannula, a catheter, or other form of hollow fluid transport means, inserted e.g. via a removable needle, and adapted to deliver doses of a medicament.

According to one embodiment the medical device comprises an inlet and an outlet connected to a cannula, a catheter, or other form of hollow fluid transport means, for transporting a medicament or a body fluid through the medical device.

The medical device may comprise a pump for pumping the medicament from the reservoir to the injection element and thus through the injection element to the patient. The pump may be any sort of pump, e.g. a pouch pump, a peristaltic pump, a membrane pump, an electro osmotic pump, a micropump, as known in the art, adapted for delivery of a medicament.

An "energy-receiving unit" is a mechanism in the medical device designed to interact with a mechanism in the hand-held device called "energy-transfer unit", when medicament treatment is specifically requested via the hand-held device and when the relative positioning of the medical device and the hand-held device is such that the energy-receiving unit and the energy-transfer unit are in an energy-transfer position and this position has been verified. In this way, transfer of energy for medical treatment is prevented to occur, until the energy-receiving unit and the energy-transfer unit are not in the energy transfer-position such that the energy-receiving unit is enabled to receive in a specific and secure manner from the energy-transfer unit of the hand-held device the correct amount and form of energy required for the intended medical treatment.

According to certain embodiments the energy-receiving unit comprises at least one pump rotor and/or a primary rotor transferring rotational force to the at least one pump rotor, e.g. via a gear mechanism, a spring mechanism, a belt mechanism, wherein the pump rotor is adapted to transform rotational force into pumping force when rotating around an axis. The pump rotor may be a rod or pin-like element. It may be connected to the pump if present, e.g. directly inserted into the pump or have the form of a disc or the like directly attached to the pump or connected to it, e.g. via a gear mechanism.

According to one embodiment, the energy-receiving unit comprises at least one axial pump element for transforming axial force into pumping force. The axial pump element may be a plunger-like, a screw-like or any push or pull element, as well as any adapter coupled to a push element, adapted to apply axial force. The axial pump element may be directly attached to the pump, if present, or connected to the pump, e.g. adapted to apply axial force on another element of the pump. According to one embodiment the axial pump element is adapted to apply axial force on the liquid contained in the reservoir, the reservoir being e.g. a syringe or a compressible chamber, pouch, pocket, blister, tube, coil or the like.

According to one embodiment the energy-receiving unit comprises at least one valve for opening or closing a fluid passage or varying the flow of liquid through a least one passage or channel. The energy-receiving unit may comprise a valve rotor and/or an axial valve element for transforming rotational force and/or axial force into rotational and/or axial movement for opening/closing the valve or regulating the amount of opening of the valve.

An axial pump or valve element may be adapted to move in alternate directions along an axis. In applying the axial force, the axial pump or valve element may be adapted to vibrate or oscillate, i.e. the axial force may be vibrational or oscillatory. According to one embodiment the axial pump or valve element is a membrane. According to another embodiment the axial pump element comprises a piezo element.

In general one or more axial elements may be connected to one or more rotors so that rotational force may be transformed into axial force and vice versa.

Also, an axial element may rotate before and/or during and/or after movement in axial direction. Analogously, a rotor may move in axial direction before and/or during and/or after rotation. This means that a rotor may also work as an axial element and an axial element may also work as a rotor.

The term rotation is used here generically to indicate any number of revolutions or fractions of a revolution without limit of time. Also, rotation may occur in opposite or alternate directions, with constant motion, accelerated motion, or pulse.

According to one embodiment the energy-receiving unit comprises a safe-lock mechanism. A "safe-lock mechanism" is a mechanism, which prevents any one or more rotors to rotate and/or axial elements to move in any direction. It may be embodied as an occluding element, which occludes the passage of medicament from the reservoir to the injection element, until this mechanism is unlocked by the energy-transfer unit of the hand-held device. The safe-lock mechanism thus contributes to prevent that medicament treatment occurs accidentally when not required, e.g. that medicament is delivered when not required, e.g. due to possible interferences, e.g. due to energy received by undesired energy sources, e.g. present in the environment.

The safe-lock mechanism may comprise a locking element such as an insertable/retractable rod or finger or an L-shaped or comb-shaped pivotable arm with one or more teeth, designed e.g. as a clamp, which can assume either of two positions, an engaged or tight position when it is in a locked status and a retracted or enlarged position when it is in an unlocked status. The locking element may be made e.g. of a plastic or metallic material, designed to fit e.g. between the teeth of a saw-like or screw-like edge or cavity at the edges of any rotor or axial element, and may comprise a spring, e.g. to return to the locked status after being unlocked, or it may be itself flexible or elastic, e.g. capable of being stretched and to return to its original position afterwards. According to one embodiment the safe-lock mechanism is configured as an axial element or a rotor, e.g. a primary rotor, which needs to move in axial direction and engage with e.g. a pump rotor before rotational force can be transferred to the pump rotor and hence transformed into pumping force.

Alternatively, the pump rotor itself may need to be pushed or pulled in the axial direction before freedom to rotate is provided.

According to one embodiment the at least one safe-lock mechanism comprises at least one ferromagnetic element or a magnet or a coil. The magnet may be for example a permanent magnet or a combination of different permanent magnets arranged e.g. to form a specific magnetic configuration, so that for example only a specific corresponding magnetic field can be used to unlock the safe-lock mechanism.

According to one embodiment the safe-lock mechanism comprises an electronic chip encoder adapted to encode an electromagnetic signal from the hand-held device for unlocking the safe-lock mechanism.

The system may be configured to unlock the safe-lock mechanism only after verification that the energy-transfer unit and the energy-receiving unit are in an energy-transfer position. Alternatively, the unlocking of the locking element by the hand-held device may be used to verify that the energy-transfer position has been reached. In particular, the system may be configured such that the energy-transfer unit is instructed to transfer energy to the energy-receiving unit needed for medical treatment only after verification that the safe-lock mechanism has been unlocked.

According to one embodiment the energy-receiving unit comprises at least one directional element, allowing any one or more rotors to rotate in a preferred direction, and/or one or more axial elements to move in a preferred direction. The directional element may be for example an inclined flexible elastic tongue or palette made e.g. of a plastic or metallic material, fitting e.g. between the teeth or grooves of a saw-like or screw-like edge of any rotor or axial element.

According to one embodiment any one or more rotors and/or axial elements, comprises at least one magnet or a ferromagnetic element.

In general, the energy-receiving unit may comprise at least one element for transforming energy received by the energy-transfer unit into mechanical force, e.g. rotational and/or axial force, and/or into electric current, wherein said at least one element is chosen from the group of at least one magnetic element, at least one ferromagnetic element, at least one coil, adapted e.g. to operate with a modulated signal frequency and/or intensity, at least one electromagnetic resonator, at least one photoelectric cell, at least one sound transducer.

The magnet may be for example a permanent magnet or a combination of different permanent magnets arranged e.g. to form a specific magnetic configuration.

According to one embodiment the energy-receiving unit comprises at least one stabilization element for minimizing the moment of tilt, that is to minimize inclinations of the axis, of any one or more rotors and/or axial elements, while still rotation and/or movement in the axial direction is allowed. The stabilization element may be for example a primary rotor concentrically arranged with respect to a pump rotor wherein the primary rotor is allowed to incline its axis within a tolerance range without causing an inclination of the axis of the pump rotor. The stabilization element or part of the stabilization element may be also a carved compartment or chamber so designed to fit the outer dimensions or footprint of a rotor or axial element. According to another embodiment the stabilization element may have the form of a cavity or groove into which a part, e.g. a pin, extending from a rotor or axial pump element, may fit. Alternatively the cavity may be on any one or more of the rotors or axial elements and into which a stabilization element, e.g. a pin or protrusion in the housing of the medical device fits.

In order to perform medical treatment, e.g. in order to deliver a dose of medicament, the energy-receiving unit needs to be activated. "Activating the energy-receiving unit" may comprise unlocking one or more safe-lock mechanisms. "Activating the energy-receiving unit" may comprise transferring rotational force to at least one rotor and/or axial force to at least one axial element of the energy-receiving unit. "Activating the energy-receiving unit" may comprise providing electric power to the medical device, e.g. by induction.

The system of the present invention further comprises a hand-held device. The energy source required to activate the energy-receiving unit comes from the energy-transfer unit of the separate hand-held device, typically without any energy source being present in the medical device itself. This is distinguished from mere wireless systems, which just transfer a command in the form of an electromagnetic signal to the medical device to perform the medical treatment but not the energy itself needed for performing the medical treatment.

A "hand-held device" is thus an energy source for the medical device, for transferring to the medical device at least part of the energy needed for performing medical treatment. "At least part of the energy" means that the medical device may according to one embodiment, e.g. if comprising one re-usable component and one disposable component, comprise an energy source used, e.g. for activating in part the energy-receiving unit or for performing a base medical treatment, but that energy from the energy-transfer unit is nevertheless needed for completing the activation or for adjusting the medical treatment or performing an additional medical treatment. For example, the medical device may be adapted to deliver a continuous flow of medicament powered by an internal energy source but also adapted to receive energy from the energy-transfer unit to deliver a supplementary dose of medicament or adjusting the flow of medicament. According to one embodiment, the medical device comprises an osmotic pump adapted to deliver a continuous flow of medicament and adapted to receive energy from the energy-transfer unit, e.g. in the form of induced current in order to change, at least temporarily, the flow rate of the medicament, e.g. for temporarily delivering a larger volume of medicament per time unit.

A "hand-held device" is also a control device, which enables to perform medical treatment, e.g. to deliver a dose of medicament when it is requested by providing the correct amount and form of energy to the energy-receiving unit of the medical device when medicament treatment is specifically requested via the hand-held device and when the relative positioning of the medical device and the hand-held device is such that the energy-receiving unit and the energy-transfer unit are in an energy-transfer position and this position has been verified. A "hand-held device" is also an interface device enabling the user, e.g. the patient and/or a technician/doctor/care giver to interact with the medical device. The hand-held device enables for example to set the amount of a medicament dose, to verify that the conditions for delivery of such dose are satisfied, and to alert the user should any atypical situation occur in the procedure or to react to an atypical situation, by suggesting or executing a remedy operation. Thus all or most electronic components, such as e.g. a processor, a memory, switch and operational buttons, electric circuits, printed circuit board, wires, a visual and/or Braille-like display, a battery or other form of power supply, one or more ports for recharging and/or for connecting to other devices, e.g. a computer, e.g. for exchanging data, alert or warning signal emitters, are integrated on the separate hand-held device rather than on the delivery device. The delivery device thus remains simple, small and cheap. A hand-held device may have additional functions. It may be for example adapted as a body parameter meter, e.g. as a glucose meter, e.g. to monitor the response to the medical treatment. It may comprise even functions such as a telephone, a gps, etc. . . . The hand-held device may be a common interface device for several medical devices of the same or different type and/or for different patients. The hand-held device is therefore intended as a separate device with respect to the medical device, distinguished e.g. from the re-usable component of a two-component medical device, which needs to be fixedly coupled to the disposable component for the entire duration of use of the medical device. The hand-held device is also distinguished from mere wireless hand-held devices providing just an exchange of data or commands between the hand-held device and the medical device. According to the present invention, the hand-held device is an energy source for performing the medical treatment and it needs to be temporarily positioned in a particular energy-transfer position for transferring to the medical device the energy needed for the medical treatment.

The hand-held device thus comprises an energy-transfer unit. An "energy-transfer unit" is a mechanism, which enables the hand-held device to transfer the correct amount and form of energy to the energy-receiving unit of the medical device when medicament treatment is specifically requested via the hand-held device and when the relative positioning of the medical device and the hand-held device is such that the energy-receiving unit and the energy-transfer unit are in an energy-transfer position and this position has been verified.

According to one embodiment the energy-transfer unit comprises at least one unlocking element for unlocking the at least one safe-lock mechanism of the control unit when the energy-receiving unit and the energy-transfer unit are in the energy-transfer position.

According to one embodiment the unlocking element comprises at least one magnet. The magnet may be for example a permanent magnet or a combination of different permanent magnets, or an electromagnet, e.g. a coil capable of generating a magnetic field, which interacts with the at least one ferromagnetic element or magnet or coil comprised in the safe-lock mechanism. Such interaction between magnetic field generated by the unlocking element and magnet or magnets or coils comprised in the safe-lock mechanism may be specific, or modulated, meaning that only in presence of the magnetic field generated by the unlocking element and only in the energy-transfer position the safe-lock mechanism can be unlocked as with a key, while it remains in the locked status in the presence of other magnetic fields which may be encountered in the environment. This specific activation may thus introduce a further safety measure in the use of the delivery device.

The energy-transfer unit comprises a drive unit providing rotational force and/or axial force to any one or more rotors and/or axial elements or electric current by induction when the energy-receiving unit and the energy-transfer unit are in the energy-transfer position.

The drive unit may comprise electromagnets or a drive rotor or a drive element connected to a motor, the drive rotor or drive element comprising at least one magnet. The magnet may be for example a permanent magnet or a combination of different permanent magnets arranged e.g. to generate a specific magnetic field.

In general, the energy-transfer unit may comprise at least one element chosen from the group of at least one electromagnet, at least one permanent magnet, at least one coil, at least one electromagnetic resonator, at least one sound emitter, at least one light emitting element, for transferring energy to the energy-receiving unit.

The unlocking element and the drive unit may cooperate synergistically to activate the energy-receiving unit in a specific manner as a key.

The "energy-transfer position" is defined as a tree-dimensional space boundary, into which the energy-transfer unit and the energy-receiving unit must be in order to enable the transfer of a sufficient amount of energy, which is needed for performing medical treatment, from the energy-transfer unit to the energy-receiving unit, wherein in the energy-transfer position the hand-held device is separated from the medical device. The hand-held device and the medical device therefore need to be placed within a certain space tolerance range, which is favorable to the transfer of energy, i.e. at a certain distance and with a certain orientation or angle, with respect to each other in order for the transfer of energy to be enabled. The energy needed for performing medical treatment is the energy needed for activating the energy-receiving unit.

The system further comprises at least one position sensor. A "position sensor" is a device that permits the detection of the energy-transfer position by detecting the relative position of the hand-held device and the medical device with respect to each other, in particular the relative position of the energy-transfer unit and the energy-receiving unit with respect to each other. It can either be an absolute position sensor or a displacement sensor. It can be either a linear or an angular position sensor or both, i.e. adapted to measure the relative distance between two points or surfaces and/or the relative orientation or angle with respect to a surface or axis of reference. The at least one position sensor may be configured to detect the relative position of the energy-transfer unit and the energy-receiving unit when moving the medical device and the hand-held device with respect to each other, e.g. when moving the hand-held device towards the medical device, such as to guide the user towards the energy-transfer position. The position sensor may be calibrated according to the desired sensing range, e.g. below 10 cm or even below 5 cm. In general, the at least one position sensor is adapted to detect at least when the energy-transfer unit and the energy-receiving unit are in the energy-transfer position. This means, that the at least one position sensor may be configured to detect only the energy-transfer position as end position.

The position sensor may comprise a gyroscope, e.g. a MEMS (Microelectromechanical systems) gyroscope.

The position sensor typically comprises at least a first sensor component in the medical device, which is adapted to be detected by at least a second sensor component in the hand-held device.

In general, the term "in the medical device" or "in the hand-held device" is herein used to indicate that the object referred to is part of or belongs to, e.g. specifically associated with, the medical device or the hand-held device respectively, either inside or outside, e.g. on the housing, or otherwise coupled to.

According to one embodiment, the position sensor is a proximity sensor, able to detect the presence and preferably the distance of a proximity target without physical contact.

For example, the first sensor component may comprises at least one metal proximity target and the second sensor component may be an inductive sensor, which is adapted to detect the at least one metal target, by measuring the variation of current in a coil.

Other types of proximity sensors may however be also employed. For example, the second sensor component may be a capacitive or photoelectric sensor, adapted to detect another type of proximity target, e.g. a materially distinguishable component or an electric resistance, by emitting a beam of electromagnetic radiation (infrared, for instance), and measuring changes in the field or return signal.

According to one embodiment the first sensor component comprises at least one magnet or an electromagnet and the second sensor component is a Hall effect sensor, i.e. a transducer that varies its output voltage in response to the magnetic field of the first sensor component. The magnetic field may be induced by inducing a current in a coil, e.g. by a magnetic field generated by the energy-transfer unit.

In general, the at least one first sensor component may comprise at least one element chosen from the group of at least one magnetic element, at least one ferromagnetic element, at least one coil, at least one electromagnetic resonator, at least one photoelectric cell, at least one sound transducer, adapted to be detected by the at least one second sensor component and/or for receiving energy from the energy-transfer unit needed for being detected by the at least one second sensor component, e.g. for emitting a return signal.

In general, the at least one second sensor component comprises at least one element chosen from the group of a force meter, at least one electromagnet, at least one permanent magnet, at least one coil, at least one electromagnetic resonator, at least one sound emitter, at least one light emitting element, for detecting the at least one first sensor component.

The system may comprise a plurality of position sensors of the same or different type, e.g. a combination of different position sensors.

According to one embodiment the system comprises at least one feedback sensor for detecting, when the energy-transfer unit and the energy-receiving unit are in the energy-transfer position, at least one situation chosen from the group of end of dose, correct or incorrect dose delivered, amount of energy used for medical treatment, error in the medical device, occlusion of the medical device, exhaustion of medicament, leak of medicament. The feedback sensor typically comprises at least a first feedback sensor component in the medical device, which is adapted to be detected by at least a second feedback sensor component in the hand-held device, wherein the first feedback sensor component may comprises at least one element chosen from the group of at least one magnetic element, at least one ferromagnetic element, at least one coil, at least one electromagnetic resonator, at least one photoelectric cell, at least one sound transducer, for being detected by the at least one second sensor component and/or for receiving energy from the energy-transfer unit needed for being detected by the at least one second sensor component and wherein the at least one second sensor component may comprise at least one element chosen from the group of a force meter, at least one electromagnet, at least one permanent magnet, at least one coil, at least one electromagnetic resonator, at least one sound emitter, at least one light emitting element, for detecting the at least one first sensor component.

According to one embodiment the system comprises an identification sensor for detecting the identity of the medical device by the hand-held device, e.g. during the guiding of the hand-held device and the medical device into the energy-transfer position or when the energy-transfer unit and the energy-receiving unit are in the energy-transfer position. The identification sensor may be used to check e.g. the lot number or expiry date and to verify that energy needed for medical treatment is transferred to the correct medical device, in case e.g. the same hand-held device is configured to be used with different types of medical devices, or is configured to be used with different patients, which may require different medical treatment, e.g. different doses.

The identification sensor may be for example an RFID chip in the medical device adapted to be detected by the hand-held device. According to one embodiment, the at least one position sensor also functions as identification sensor, wherein the correct positioning, i.e. detection of the energy-transfer position, may be indication of correct identity.

The energy-receiving unit and the energy-transfer unit may share components with the at least one position sensor. This means that one or more elements of the energy-receiving unit chosen from the group of at least one magnetic element, at least one ferromagnetic element, at least one coil, at least one electromagnetic resonator, at least one photoelectric cell, at least one sound transducer may function also as a first sensor component. Analogously, one or more of the energy-transfer unit elements chosen from the group of at least one electromagnet, at least one permanent magnet, at least one coil, at least one electromagnetic resonator, at least one sound emitter, at least one light emitting element, may function also as second sensor component.

For example, a magnetic element in the energy-receiving unit used to unlock the safe-lock mechanism when receiving energy from the energy-transfer unit may function also as first sensor component for a hall sensor or force meter in the hand-held device to verify that the energy transfer position has been reached.

Also the feedback sensor may share components with the energy-receiving unit and/or the energy-transfer unit and/or with the at least one position sensor. This means that one or more elements of the energy-receiving unit and/or of the energy-receiving unit and/or of the at least one position sensor may function also as feedback sensor elements.

For example, the second feedback sensor component may be a Hall sensor monitoring the variation of magnetic field caused by the movement of a first feedback sensor component in the energy-receiving unit, e.g. the rotation of a pump rotor comprising at least one magnetic element.

According to one embodiment, the system comprises at least one attractive force generating element for generating attractive force between the hand-held device and the medical device such as to guide the positioning of the hand-held-device with respect to the medical device until the energy-transfer unit and the energy-receiving unit are in the energy-transfer position and/or to facilitate holding of the energy-transfer position for the duration of the medical treatment. For example, the at least one attractive force generating element may be activated once the energy-transfer position has been reached in order to facilitate holding of the energy-transfer position for the duration of the medical treatment.

The attractive-force generating element may comprise for example at least one permanent magnet or ferromagnetic target in the medical device and at least one permanent magnet or electromagnet in the hand-held device, preferably at least one ferromagnetic target in the medical device and at least one corresponding electromagnet in the hand-held device.

According to one embodiment, the housing of the hand-held device in correspondence to the energy-transfer unit is shaped as to form a complementary cavity into which at least a part of the medical device comprising the energy-receiving unit substantially fits when the energy-transfer unit and the energy-receiving unit are in the energy transfer position, while leaving sufficient space e.g. for one or more layers of clothing to be sandwiched in between. The term "substantially" is also utilized herein to represent the degree by which a quantitative representation may vary from a stated reference without resulting in a change in the basic function of the subject matter at issue.

According to one embodiment, the position of the energy-transfer unit is adjustable with respect to the housing of the hand-held device in order to facilitate or to make the achievement of the energy-transfer position possible, or in order to reach faster the energy transfer position, e.g. in situations where positioning is particularly difficult, e.g. in case of implanted medical devices or medical devices in a non easily accessible part of the body, e.g. under the clothes, or in case of different positions of the energy-receiving unit in different medical devices. "Adjustable" means that the energy-transfer unit or a part of it, e.g. at least the drive unit or an unlocking element, is connected by an articulated or flexible joint to the hand-held device such as to be tiltable and/or rotatable and/or translatable with respect to the housing of the hand-held device, such as to match the position, orientation or angle of the energy-receiving unit, and resulting in the energy-transfer position. The energy-transfer unit may also be adapted to change shape, e.g. to expand or contract, e.g. according to the size of the energy receiving unit, if e.g. medical devices of different sizes are used with the same hand-held device.

The hand-held device comprises also a controller. A "controller" is a computing unit, embodied e.g. as a programmable logic controller running a computer-readable program provided with instructions to perform operations in accordance with one or more process operation plans. The controller is configured to control the energy-transfer unit such that energy needed for medical treatment is transferred from the energy-transfer unit to the energy-receiving unit only when the energy-transfer unit and the energy-receiving unit are in the energy-transfer position. In particular, the controller is programmed to receive positioning information from the at least one position sensor, to compare such positioning information with stored reference positioning information related to the energy-transfer position, to identify from this comparison if and when the energy-transfer position has been reached and only then to enable the energy-transfer unit to transfer energy needed for medical treatment to the energy-receiving unit.

According to one embodiment the controller is programmed to determine, e.g. when medical treatment is requested, the actual relative position of the hand-held device with respect to the medical device, particularly the actual relative position of the energy-transfer unit with respect to the energy-receiving unit, and to guide the positioning of the hand-held-device with respect to the medical device until the energy-transfer unit and the energy-receiving unit are into the energy-transfer position.

According to one embodiment the controller is programmed to check that the energy-transfer position is maintained during medical treatment based on continuous or periodic positioning information from the at least one position sensor during the medical treatment.

According to one embodiment the controller is programmed to activate attractive force generating elements once the energy-transfer position has been reached in order to facilitate holding of the energy-transfer position for the duration of the medical treatment.

According to one embodiment the controller is programmed to check, based on the information from the identification sensor, the identity and/or conformity of the medical device, and eventually to disable the energy-transfer unit such as to prevent that an incorrect or non-conform medical device, e.g. expired or intended for another patient or medical treatment is used. In case that the hand-held device is adapted as common interface device for different patients and/or for different medical devices, the controller may be programmed such that, after checking the identity of the medical device, it provides instructions to execute respective process operation plans for the different medical devices and/or patients. Thus, the controller may be programmed to provide instructions to execute patient or medical device specific operation plans. The controller may be programmed to provide instructions to execute also a general process operation plan, which is common, at least in part, for different medical devices and/or patients. Analogously, the controller may be connected to a memory chip such as an EPROM to record and/or retrieve data related to one or more medical devices and/or one or more patients. In particular, the memory chip may be set up to keep a register or protocol, e.g. related to each use of one or more medical devices. Also, the controller and the memory chip may be set up to display, e.g. via a display, the information stored in the memory chip, and/or to transfer the information to and/or receive information from an external management device, such a smart phone, a tablet or mobile computer, a desktop computer, or another hand-held device of the same or different type, e.g. via wired or wireless connection.

According to one embodiment, the controller is programmed to adjust the position of the energy-transfer unit with respect to the housing of the hand-held device, based on information from the at least one position sensor and/or from the identification sensor.

According to one embodiment the system, e.g. the hand-held device, comprises at least one signal emitter adapted to emit at least one identifiable signal when the energy-transfer unit and the energy-receiving unit are in the energy-transfer position or out of the energy-transfer position and/or during guiding of the energy-transfer unit and the energy-receiving unit into the energy-transfer position and/or during medical treatment. The signal emitter may be for example a light source or a display for emitting a visual signal or message. The signal may be however in alternative or in addition also acoustic and/or vibrational.

In particular, the controller, based on the information from the at least one position sensor, may be programmed to enable the signal emitter to emit an identifiable signal to inform the user that the energy-transfer unit and the energy-receiving unit are in the energy-transfer position. The controller may be either programmed to enable the energy-transfer unit to activate the energy-receiving unit once the energy-transfer position has been confirmed or it may be programmed to enable the signal emitter to emit an energy-transfer position confirmation signal and wait for user instructions before enabling the energy-transfer unit to activate the energy-receiving unit.

The controller may be programmed to enable the signal emitter to emit an identifiable signal to inform the user of the actual relative position of the energy-transfer unit and the energy-receiving unit during guiding of the energy-transfer unit and the energy-receiving unit into the energy-transfer position. The signal may be for example increasing in intensity and/or frequency when the energy-transfer unit and the energy-receiving unit become closer to the energy transfer position. The signal emitter may comprise a plurality of individually switchable luminous signals emitters, e.g. arranged according to a regular geometry, e.g. a circle, and adapted to indicate the direction of movement of the hand-held device according to their switching mode, e.g. on/off or change of color. The achievement of the energy-transfer position may be indicated e.g. by all luminous signal emitters in the on mode or showing the same color.

The controller may be programmed to enable the signal emitter to emit an identifiable signal, e.g. a continuous or periodic confirmation signal to inform the user and make sure that the energy transfer position is maintained during medical treatment. In particular, the controller may be programmed to enable the signal emitter to emit an identifiable signal to inform the user that the energy-transfer unit and the energy-receiving unit are out of the energy-transfer position and eventually to disable the energy-transfer unit if e.g. the energy-transfer position cannot be reached or if it is lost during the medical treatment.

The same or different signal emitter may be configured to emit a feedback signal, when the energy-transfer unit and the energy-receiving unit are in the energy-transfer position, with respect to at least one situation chosen from the group of end of dose, correct or incorrect dose delivered, amount of energy used for medical treatment, error in the medical device, occlusion of the medical device, exhaustion of medicament, leak of medicament. In particular, the controller, after verification that the energy-transfer unit and the energy-receiving unit are in the energy transfer position, may be programmed to enable the signal emitter, based on the information from at least one feedback sensor, to emit an identifiable feedback signal to inform the user that a particular situation not related to positioning, before, during or after medical treatment, has occurred.

The same or different signal emitter may be configured to emit a medical device conform or non-conform signal with respect to the medical device, based on the information from the identification sensor.

The present invention also refers to a method of controlling by the hand-held device the medical device. The method comprises the step of detecting when the energy-transfer unit and the energy-receiving unit are in the energy-transfer position. The method further comprises the step of transferring energy needed at least in part for performing medical treatment from the energy-transfer unit to the energy-receiving unit when the energy-transfer unit and the energy-receiving unit are in the energy-transfer position. The method may comprise the steps of receiving positioning information from at least one position sensor, comparing such positioning information with stored reference positioning information related to the energy-transfer position, identifying from this comparison if and when the energy-transfer position has been reached and only after the energy-transfer position has been reached enabling the energy-transfer unit to transfer energy needed for medical treatment to the energy-receiving unit.

The method may comprise the step of determining the actual relative position of the hand-held device with respect to the medical device, particularly the actual relative position of the energy-transfer unit with respect to the energy-receiving unit, and emitting guiding signals for guiding the energy-transfer unit and the energy-receiving unit into the energy-transfer position.

The method may comprise the step of checking by an identification sensor the identity and/or conformity of the medical device before energy is transferred. The method may comprise the step of emitting a medical device conform or non-conform signal with respect to the medical device.

The method may comprise the step of adjusting the position of the energy-transfer unit with respect to the housing of the hand-held device.

The method may comprise the step of verifying that the energy-receiving unit is unlocked such as to be able to receive energy needed at least in part to perform medical treatment.

The method may further comprise the step of transforming the transferred energy into mechanical force, e.g. rotational and/or axial, and/or into electric current.

The method may comprise the step of checking that the energy-transfer unit and the energy-receiving unit are in the energy-transfer position during the transfer of energy from the energy-transfer unit to the energy-receiving unit.

The method may comprise the step of emitting at least one identifiable signal when the energy-transfer unit and the energy-receiving unit are in the energy-transfer position or out of the energy-transfer position and/or during guiding of the energy-transfer unit and the energy-receiving unit into the energy-transfer position and/or during medical treatment.

The method may comprise the step of disabling the energy-transfer unit if e.g. the energy-transfer position cannot be reached or if it is lost during the medical treatment or if an incorrect or non-conform medical device is used.

The method may comprise the step of detecting before, during or after medical treatment and after the energy-transfer position has been verified, at least one situation not related to positioning, such as end of dose, correct or incorrect dose delivered, amount of energy used for medical treatment, error in the medical device, occlusion of the medical device, exhaustion of medicament, leak of medicament.

The method may comprise the step of emitting a feedback signal and/or disabling the energy-transfer unit, before, during or after medical treatment and after the energy-transfer position has been verified, with respect to at least one situation not related to positioning, such as end of dose, correct or incorrect dose delivered, amount of energy used for medical treatment, error in the medical device, occlusion of the medical device, exhaustion of medicament, leak of medicament.

More in detail the present invention is explained with reference to the following drawings representing schematically exemplary embodiments.

FIG. 1 depicts schematically and not to scale a system 300 for medical treatment, in this case for the trans-dermal delivery of doses of a medicament. The system 300 comprises a medical device 100 and a hand-held device 200. The medical device 100 and the hand-held device 200 are shown in the energy transfer-position. The medical device 100 comprises a reservoir 101 for holding a medicament to be delivered, a trans-dermal injection element 102 for delivering doses of the medicament and an energy-receiving unit 120. One function of the energy-receiving unit 120 is that to transform energy received from the hand-held device 200 into pumping force for pumping doses of the medicament from the reservoir 101 to the trans-dermal injection element 102, thereby performing medical treatment. The hand-held device 200 comprises a housing 201 and an energy-transfer unit 220 for transferring energy needed for the medical treatment to the energy-receiving unit 120 of the medical device 100. The hand-held device 200 comprises elements needed for operation and control, e.g. electronic components such as a printed circuit board (not shown), a battery 240, a port 250 for recharging and/or for connecting to other devices, e.g. for exchanging data, e.g. to a computer, e.g. wirelessly, buttons or switches 260 located on the housing 201 and a display 270 also adapted as visual signal emitter. The system 300 further comprises position sensors 231,131 and in particular first position sensor components (position sensor targets) 131 in the medical device 100 and second position sensor components 231 in the hand-held device 200, wherein the second position sensor components 231 are adapted to detect the first position sensor components 131 thereby detecting the relative position of the energy-transfer unit 220 and the energy-receiving unit 120, comprising when the energy-transfer unit 220 and the energy-receiving unit 120 are in the energy-transfer position. The system 300 further comprises a feedback sensor 232,132 and in particular a first feedback sensor component (feedback sensor target) 132 in the medical device 100 and a second feedback sensor component 232 in the hand-held device 200. The feedback sensor 232,132 also acts as identification sensor in this case.

The hand-held device 200 further comprises a controller 230 for enabling the energy-transfer unit 220 to transfer the energy to be used for performing medical treatment to the energy-receiving unit 120 only when the energy-transfer unit 220 and the energy-receiving unit 120 are in the energy-transfer position. The controller 230 is in communication with at least the second position sensor components 231, the energy-transfer unit 220, the second feedback/identification sensor component 232 and the signal emitter 270. The controller 230 is programmed to determine, when medical treatment is requested, the actual relative position of the hand-held device 200 with respect to the medical device 100, particularly the actual relative position of the energy-transfer unit 220 with respect to the energy-receiving unit 120, and to guide the positioning of the hand-held device 200 with respect to the medical device 100 until the energy-transfer unit 220 and the energy-receiving unit 120 are into the energy-transfer position. The controller 230 is programmed to enable the signal emitter 270 to emit an identifiable signal to inform the user of the actual relative position of the energy-transfer unit 220 and the energy-receiving unit 120 during guiding of the energy-transfer unit 220 and the energy-receiving unit 120 into the energy-transfer position and finally to inform the user that the energy-transfer unit 220 and the energy-receiving unit 120 are in the energy-transfer position. The controller 230 is programmed to check, based on the information from the identification sensor 232,132 the identity and/or conformity of the medical device, and to enable the energy-transfer unit 220 to transfer energy to the energy-receiving unit 120 if the medical device 100 is conform or to disable the energy-transfer unit 220 such as to prevent the transfer of energy to the energy receiving unit 120 if the medical device 100 is non-conform. The controller 230 is programmed to check that the energy-transfer position is maintained during the medical treatment based on continuous or periodic positioning information from the second position sensor components 231. The controller 230 is programmed to enable the signal emitter 270 to emit an identifiable signal to inform the user if the energy-transfer unit 220 and the energy-receiving unit 120 are out of the energy-transfer position and to disable the energy-transfer unit 220 if the energy-transfer position cannot be reached or if it is lost during the medical treatment.

The controller 230, after verification that the energy-transfer unit 220 and the energy-receiving unit 120 are in the energy transfer position, is programmed to enable the signal emitter 270, based on the information from the second feedback sensor component 232, to emit an identifiable feedback signal to inform the user in case a particular situation, before, during or after medical treatment, has occurred, such as end of dose, correct or incorrect dose delivered, amount of energy used for medical treatment, error in the medical device 100, occlusion of the medical device 100, exhaustion of medicament, leak of medicament.

Figure 2:
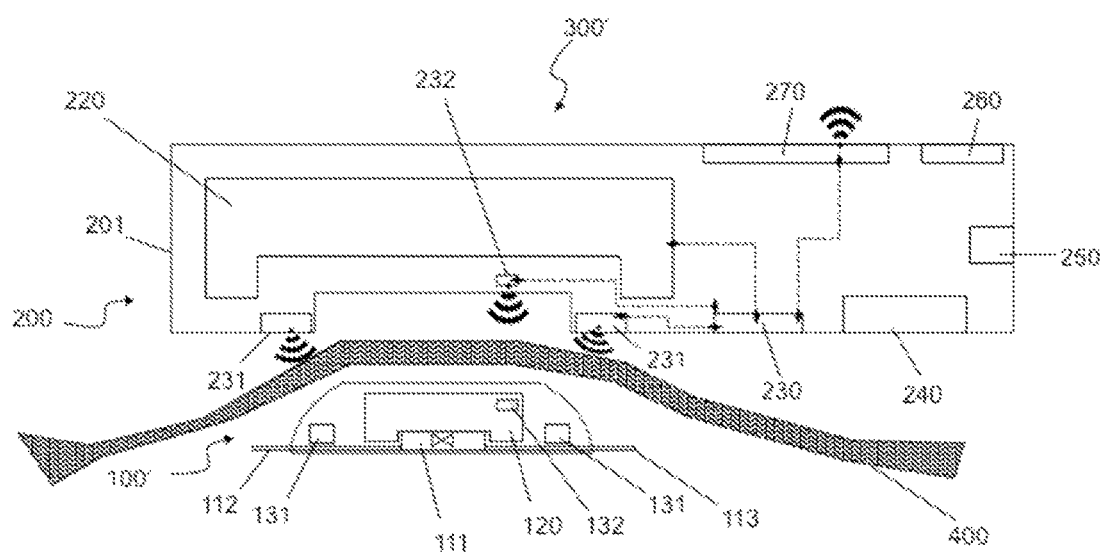
FIG. 2 depicts schematically a variant of the system of FIG. 1 wherein the system comprises a different type of medical device.

FIG. 2 depicts schematically a system 300' for medical treatment, which is a variant of the system 300 of FIG. 1. In particular, the system 300' comprises the same hand-held device 200 of FIG. 1 but a different type of medical device 100'. The difference between the medical device 100 and the medical device 100' is that the medical device 100' is an implantable medical device, depicted for clarity under a cutaneous layer 400 in FIG. 2. The medical device 100' is embodied as a valve device comprising a valve unit 111 fluidically connected to an inlet channel 112 and an outlet channel 113 and adapted to enable/disable fluid flow or vary the flow rate of a body fluid between inlet channel 112 and outlet channel 113. Medical treatment results in this case from regulation of the valve unit 111 by transferring energy from the energy-transfer unit 220 to the valve unit 111 via the energy-receiving unit 120.

Figure 3:
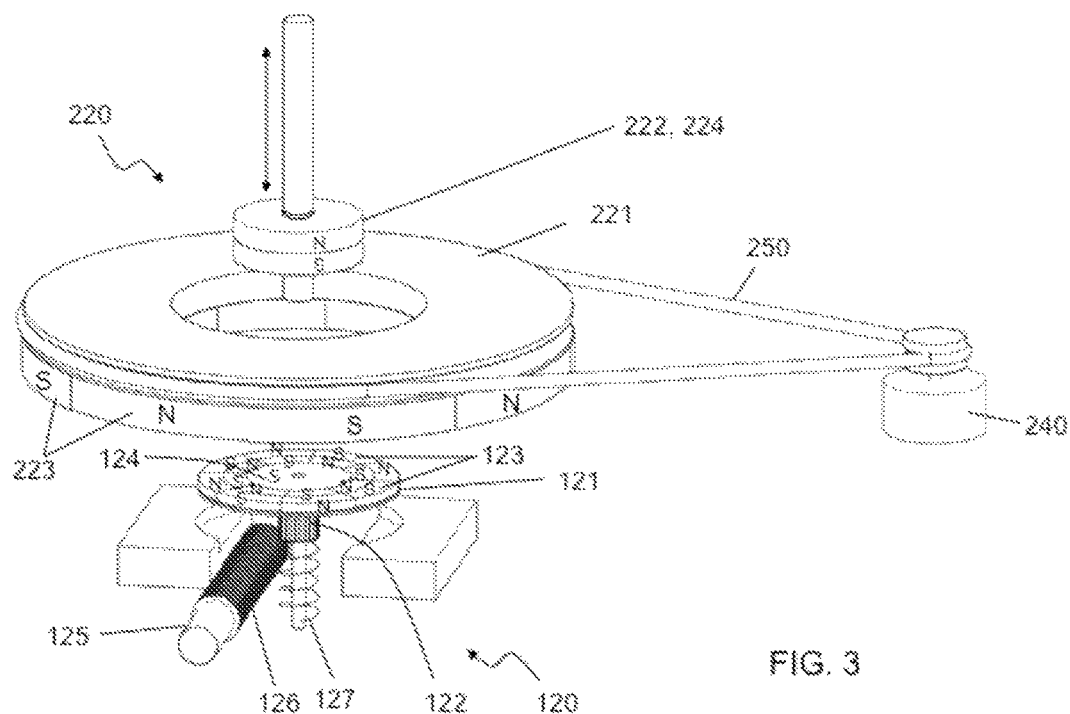
FIG. 3 depicts schematically an example of energy-transfer unit and energy-receiving unit in the energy-transfer position.

FIG. 3 depicts schematically an example of energy-transfer unit 220 and energy-receiving unit 120 in the energy-transfer position. The energy-receiving unit 120 comprises a pump rotor 121 designed to engage with an axial pump element 125 and to transform rotational force into axial force used for the medical treatment. The axial pump element 125 is in this case the plunger of a syringe-like reservoir (not shown), comprising a medicament to be delivered. The pump rotor 121 comprises a series of permanent magnets 123, 124 arranged according to a specific magnetic configuration, indicated by the letters N and S, indicating respective magnetic poles. The magnets 123 are adapted to transform energy received from a drive unit 221 of the energy-transfer unit 220 into rotational force for rotating the pump rotor 121. The magnet 124 is adapted to transform energy received from an unlocking element 222 of the energy-transfer unit 220 into axial force for moving the pump rotor 121 in axial direction and thereby unlocking the pump rotor 121. The pump rotor 121 and the axial pump element 125 are depicted disengaged from each other (for clarity). This corresponds to a locked status as when the energy-transfer unit 220 and the energy-receiving unit 120 are out of the energy-transfer position. In this locked status, the pump rotor 121 may be allowed to rotate or prevented to rotate. In any case, it needs to be moved in the axial direction before rotational force applied to the pump rotor 121 is transferred to the axial pump element 125 and transformed into axial force. This mechanism functions therefore as a safe-lock mechanism, which requires the energy-transfer unit 220 and the energy-receiving unit 120 to be in the energy-transfer position in order to be unlocked. Unlocking the safe-lock mechanism here means moving the pump rotor 121 in axial direction in order to engage with the axial pump element 125. In particular, the pump rotor 121 comprises a gear element 122 adapted to be engageable with a gear element 126 of the axial pump element 125. A spring 127 allows the pump rotor 121 to disengage and return to its original locked status once the energy-transfer unit 220 and the energy-receiving unit 120 are no longer in the energy-transfer position.

The design of the energy-receiving unit 120 may vary. The design of the energy-transfer unit 220 may also vary in order to work with different energy-transfer units 120 respectively. In this example, the energy-transfer unit 220 comprises an unlocking element 222, comprising a permanent magnet 224 for exerting a repulsive force on the pump rotor 121 via the magnet 124 of the energy-receiving unit 120, thereby unlocking the safe-lock mechanism when the energy-receiving unit 120 and the energy-transfer unit 220 are in the energy-transfer position. The unlocking element 222 is adapted to move axially such as to get closer to or farther from the medical device 100, 100'. The energy-transfer unit 220 further comprises a drive rotor 221 connected to a motor 240 via a belt 250. The drive rotor 221 comprises a series of permanent magnets 223, arranged according to a specific magnetic configuration, indicated by the letters N and S, indicating respective magnetic poles.

The drive rotor 221 is adapted to rotate thereby providing rotational force to the pump rotor 121, when the energy-receiving unit 120 and the energy-transfer unit 220 are in the energy-transfer position. The energy-transfer unit 220 is however enabled to transfer energy needed for the medical treatment only after the controller 230 (not shown in FIG. 3) has verified that the medical device 100, 100' is conform and the energy-receiving unit 120 and energy-transfer unit 220 are in the energy transfer position. This means that at least the drive unit 221 is disabled to rotate and therefore to transfer to the pump rotor 121 energy needed for medical treatment in the form of rotational force until enabled by the controller 230. In this example, also the unlocking element 222 is disabled to move axially towards the energy-receiving unit 120 and therefore to transfer axial force to the pump rotor 121 via the magnet 124 thereby unlocking the safe-lock mechanism until enabled by the controller 230. The energy-transfer unit 220 comprises also a force meter (not shown) coupled to the unlocking element 222. In this way, the force needed to unlock the safe-lock mechanism may be measured and the force meter may be used as identification sensor or as feedback sensor, e.g. to determine whether the safe-lock mechanism or the energy-receiving unit is defective. The force meter may alternatively be used as a positioning sensor wherein a certain amount of force may be indicative of unlocked safe-lock mechanism thereby indicating that the energy-receiving unit 120 and the energy-transfer unit 220 are in the energy-transfer position.

Figure 4:
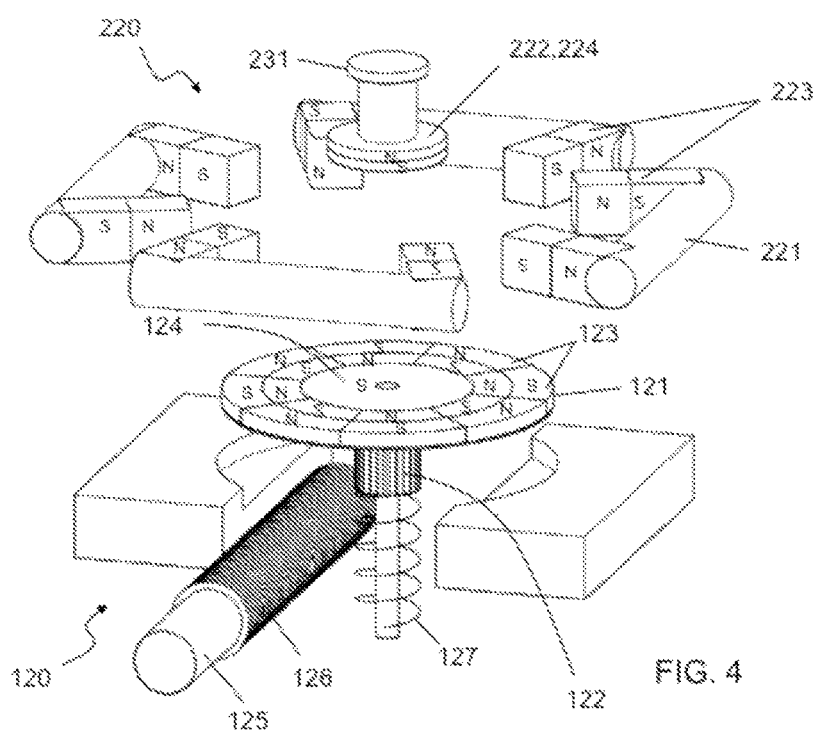
FIG. 4 depicts schematically a variant of the embodiment of FIG. 3 with a first type of position sensor.

FIG. 4 depicts a variant of FIG. 3 wherein the energy-transfer unit 220 comprises a drive rotor 221 with magnets 231 differently arranged and a fixed unlocking element 222. The unlocking element 222 comprises a permanent magnet 224 for exerting a repulsive force on the pump rotor 121 via the magnet 124 of the energy-receiving unit 120, thereby unlocking the safe-lock mechanism when the energy-receiving unit 120 and the energy-transfer unit 220 are in the energy-transfer position. The unlocking element 222 comprises also a force meter acting as position sensor 231 wherein a certain amount of force is indicative of an unlocked safe-lock mechanism thereby indicating that the energy-receiving unit 120 and the energy-transfer unit 220 are in the energy-transfer position.

Figure 5:
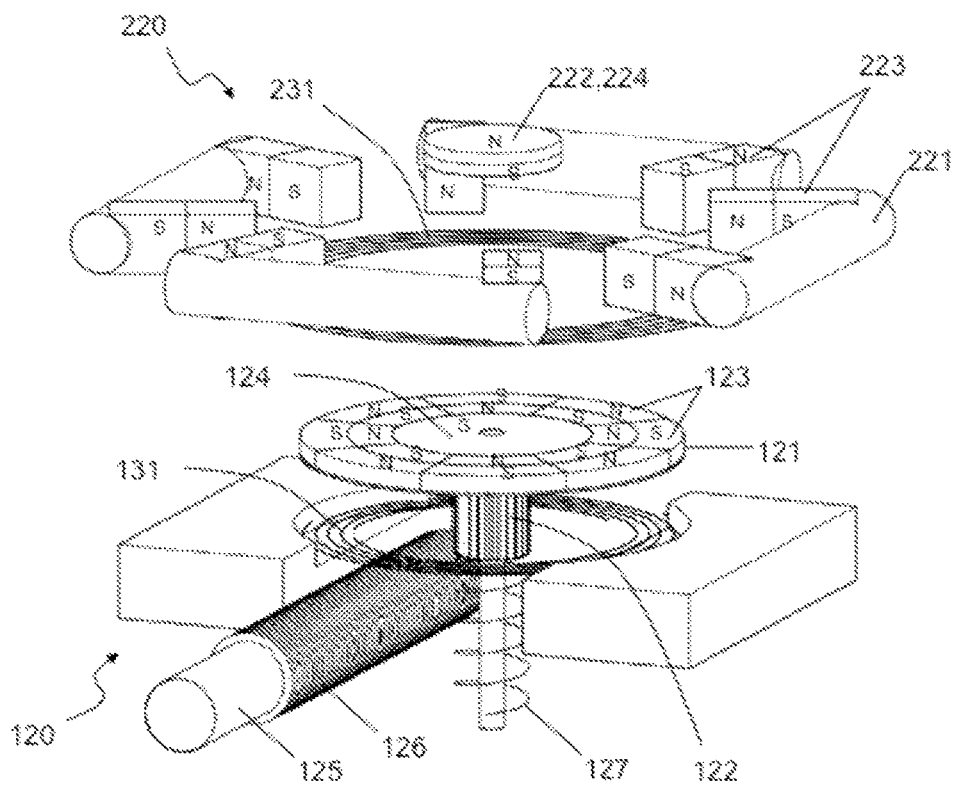
FIG. 5 depicts schematically a variant of the embodiment of FIGS. 3 and 4 with a second type of position sensor.

FIG. 5 depicts a variant of FIGS. 3 and 4 wherein the position sensor 231, 131 instead of a force meter comprises a resonator (position sensor target) 131 in the medical device 100, 100' adapted to resonate when the energy-receiving unit 120 and the energy-transfer unit 220 are in the energy-transfer position, in response to an interrogation signal, such as pulses of a low-range radio frequency transmitted by a second position sensor component 231 in the hand-held device 200. The second position sensor component 231 comprises also a receiver that is adapted to recognize whether the target 131 is resonating, thereby recognizing when the energy-receiving unit 120 and the energy-transfer unit 220 are in the energy-transfer position.

Figure 6:
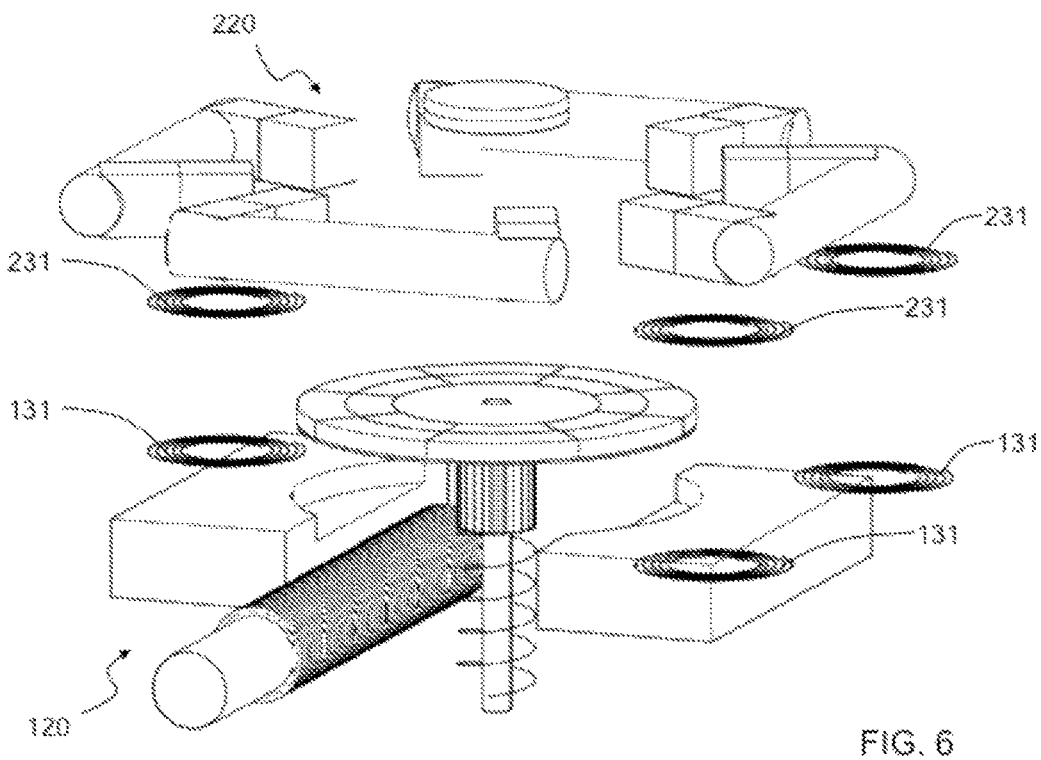
FIG. 6 depicts schematically a variant of the embodiment of FIG. 5.

FIG. 6 is a variant of the embodiment of FIG. 5 wherein the system 300 comprises a plurality of resonators 131 in the medical device 100 and respective second sensor components 231 in the hand-held device 200 arranged such as to guide the positioning of the hand-held device 200 with respect to the medical device 100, 100' until the energy-receiving unit 120 and the energy-transfer unit 220 are in the energy-transfer position.

Figure 7:
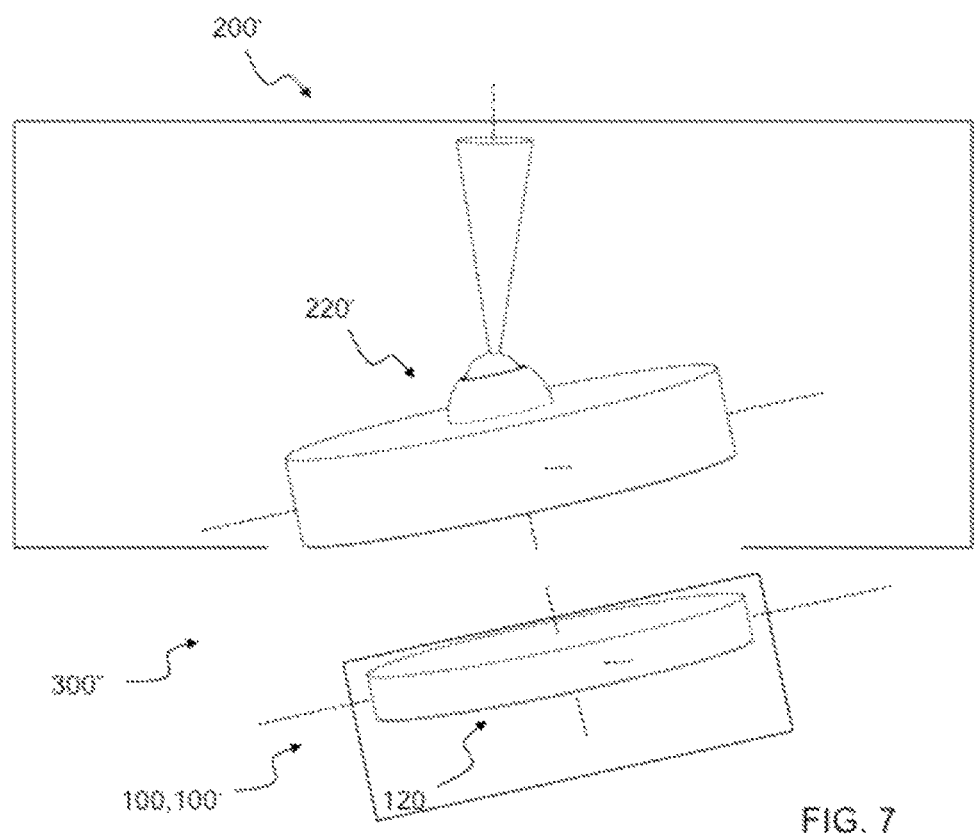
FIG. 7 depicts schematically a system similar to that of FIG. 1 or 2 comprising an adjustable energy-transfer unit.

FIG. 7 depicts schematically a system 300" similar to that of FIG. 1 or 2 comprising a hand-held device 200" with an adjustable energy-transfer unit 220'. In particular, the energy-transfer unit 220" is connected by an articulated joint to the hand-held device 200' such as to be tiltable and rotatable with respect to the housing 201 of the hand-held device 200'. Specifically, the controller 230 (not shown in FIG. 7) is programmed to adjust the position of the energy-transfer unit 220' with respect to the housing 201 of the hand-held device 200', based on information from the at least one position sensor 231, 131 (not shown in FIG. 7) such as to match the orientation and angle of the energy-receiving unit 120, and result in the energy-transfer position.

Figure 8:
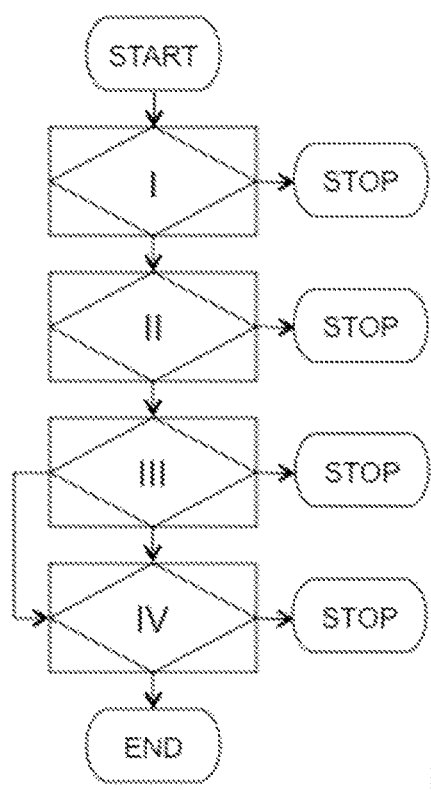
FIG. 8 is a diagram showing an example of method of controlling the medical device by the hand-held device.

FIG. 8 is a diagram showing an example of method of controlling the medical device 100, 100' by the hand-held device 200, 200'. The method comprises the step I of detecting the relative position between the energy-transfer unit 220, 220' of the hand-held device 200, 200' and the energy-receiving unit 120 of the medical device 100, 100' comprising detecting when the energy-transfer unit 220, 220' and the energy-receiving unit 100, 100' are in the energy-transfer position. Step I may comprise the step of adjusting the energy-transfer unit 220' with respect to the housing 201 of the hand-held device 200, 200' until the energy-transfer position has been reached.

Step I comprises the steps of receiving positioning information from at least one position sensor 231, 131 comparing such positioning information with stored reference positioning information related to the energy-transfer position, identifying from this comparison if and when the energy-transfer position has been reached. Step I may comprise the step of determining the actual relative position of the hand-held device 200, 200' with respect to the medical device 100, 100', particularly the actual relative position of the energy-transfer unit 220, 220' with respect to the energy-receiving unit 120, and emitting guiding signals for guiding the hand-held device 200, 200' until the energy-transfer unit 220, 220' and the energy-receiving unit 120 are into the energy-transfer position. Step I may comprise the step of emitting at least one identifiable signal when the energy-transfer position is reached and/or when the energy-receiving unit 120 and the energy-transfer unit 220, 220' are out of the energy-transfer position or the energy-transfer position cannot be reached. Step I may comprise the step of disabling or maintaining disabled the energy-transfer unit 220, 220' if the energy-transfer position cannot be reached (STOP).

Step I may comprise the step of checking by an identification sensor the identity and/or conformity of the medical device 100, 100' before energy-transfer is enabled. Step I may comprise the step of emitting a medical device conform or non-conform signal with respect to the medical device. Step I may comprise the step of disabling or maintaining disabled the energy-transfer unit 220, 220' if the medical device 100, 100' is found to be non-conform (STOP).

The method further comprises the step II of enabling the energy-transfer unit 220, 220' to transfer energy needed for medical treatment to the energy-receiving unit 120 only after the energy-transfer position has been reached and optionally after the medical device 100, 100' has been identified as conform. Step II may comprise the step of verifying that the energy-receiving unit 120, in particular the safe-lock mechanism, is unlocked such as to be able to receive energy needed at least in part to perform medical treatment and the step of disabling the energy-transfer unit 220, 220' if the safe-lock mechanism remains locked (STOP).

The method further comprises the step III of transferring energy from the energy-transfer unit 220, 220' to the energy-receiving unit 120 after the energy-transfer unit 220, 220' has been enabled, the step III comprising the step of transforming the transferred energy into mechanical force, e.g. rotational and/or axial, and/or into electric current needed for performing medical treatment. Step III may comprise the step of emitting at least one identifiable signal during the medical treatment.

Step III comprises the step of checking that the energy-transfer unit 220, 220' and the energy-receiving unit 120 are in the energy-transfer position during the transfer of energy from the energy-transfer unit 220, 220' to the energy-receiving unit 120. Step III may comprise the step of emitting an identifiable signal and/or disabling the energy-transfer unit 220, 220' if the energy-transfer position is lost during the medical treatment (STOP).

The method further comprises the step IV of detecting before, during or after medical treatment and after the energy-transfer position has been verified, at least one situation not related to positioning, such as end of dose, correct or incorrect dose delivered, amount of energy used for medical treatment, error in the medical device, occlusion of the medical device, exhaustion of medicament, leak of medicament and emitting at least one identifiable feedback signal and/or disabling the energy-transfer unit 220, 220' (END or STOP).

Of course numerous variations of the described embodiments are possible without departing from the scope of the invention. It is also noted that terms like "preferably" or "preferred" and "typically" or "typical" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

The invention claimed is:

1. A system for medical treatment comprising:
a medical device to be placed in contact with a subject, the medical device comprising
an energy-receiving unit which comprises one or more rotors and/or one or more axial elements, and
a separate hand-held device comprising
a housing, and
an energy-transfer unit adapted to transfer energy via magnetic coupling to the energy-receiving unit of the medical device only when an energy-transfer position has been reached,
a sensor adapted to detect positioning information of the energy-transfer unit relative to the energy-receiving unit, and
a controller adapted to receive the positioning information from the sensor and to compare it to reference information related to the position to be achieved to determine from the comparison whether the energy-transfer position has been reached and if so, to enable transfer of a correct amount of energy to the medical device for the medical treatment and/or to inform the subject that the energy transfer position has been reached.

2. System according to claim 1 wherein the system comprises at least one attractive force generating element for generating attractive force between the hand-held device and the medical device such as to guide the positioning of the hand-held-device with respect to the medical device until the energy-transfer unit and the energy-receiving unit are in the energy-transfer position and/or to facilitate holding of the energy-transfer position for the duration of the medical treatment.

3. System according to claim 1 wherein the controller is configured to check that the energy-transfer position is maintained during medical treatment.

4. System according to claim 1 wherein the system comprises at least one signal emitter adapted to emit at least one identifiable signal when the energy-transfer unit and the energy-receiving unit are in the energy-transfer position or out of the energy-transfer position and/or during guiding of the energy-transfer unit and the energy-receiving unit into the energy-transfer position and/or during medical treatment.

5. System according to claim 1 wherein the system comprises at least one feedback sensor for detecting, when the energy-transfer unit and the energy-receiving unit are in the energy-transfer position, at least one situation selected from the group consisting of: end of dose, correct or incorrect dose delivered, amount of energy used for medical treatment, error in the medical device, occlusion of the medical device, exhaustion of medicament and leak of medicament.

6. System according to claim 1 wherein the system comprises an identification sensor for detecting the identity of the medical device by the hand-held device during the guiding of the energy-transfer unit and the energy-receiving unit in the energy-transfer position or when the energy-transfer unit and the energy-receiving unit are in the energy-transfer position.

7. System according to claim 1 wherein the energy-receiving unit comprises at least one element selected from the group consisting of: at least one magnetic element, at least one ferromagnetic element, at least one coil, at least one electromagnetic resonator, at least one photoelectric cell and at least one sound transducer for transforming energy received by the energy-transfer unit into mechanical force and/or into electric current and wherein the energy-transfer unit comprises at least one element selected from the group consisting of: at least one electromagnet, at least one permanent magnet, at least one coil, at least one electromagnetic resonator, at least one sound emitter and at least one light emitting element, for transferring energy to the energy-receiving unit.

8. System according to claim 1 comprising at least a first sensor component in the medical device adapted to be detected by at least a second sensor component in the hand-held device.

9. System according to claim 8 wherein the at least one first sensor component comprises at least one element selected from the group consisting of: at least one magnetic element, at least one ferromagnetic element, at least one coil, at least one electromagnetic resonator, at least one photo-electric cell and at least one sound transducer, for being detected by the at least one second sensor component and/or for receiving energy from the energy-transfer unit needed for being detected by the at least one second sensor component and wherein the at least one second sensor component comprises at least one element selected from the group consisting of: a force meter, at least one electromagnet, at least one permanent magnet, at least one coil, at least one electromagnetic resonator, at least one sound emitter and at least one light emitting element, for detecting the at least one first sensor component.

10. The system according to claim 1 wherein the position of the energy-transfer unit is adjustable with respect to the housing of the hand-held device.

11. A method for controlling, by a hand-held device, a medical device to be placed in contact with a patient for medical treatment, the method comprising the steps of:
  detecting positioning information with a sensor when an energy-transfer unit of the hand-held device and an energy-receiving unit of the medical device are in an energy-transfer position by comparing the detected positioning information with reference positioning information;
  enabling the energy-transfer unit to transfer energy needed for medical treatment to the energy-receiving unit via magnetic coupling only when the energy-transfer position has been reached and/or after the patient has been notified that the energy-transfer position has been reached;
  transferring energy from the energy-transfer unit to the energy-receiving unit via magnetic coupling after the energy-transfer unit has been enabled; and
  transforming at least part of the transferred energy into rotational and/or axial mechanical force appropriate for performing the medical treatment.

12. Method according to claim 11 wherein the step of detecting when the energy-transfer unit and the energy-receiving unit are in an energy-transfer position comprises the step of verifying that the energy-receiving unit is unlocked such as to be able to receive energy via magnetic coupling needed at least in part to perform medical treatment.

13. Method according to claim 11 comprising the step of checking that the energy-transfer unit and the energy-receiving unit are in the energy-transfer position during energy-transfer from the energy-transfer unit to the energy-receiving unit.

14. Method according to claim 11 comprising the step of emitting at least one identifiable signal when the energy-transfer unit and the energy-receiving unit are in the energy-transfer position or out of the energy-transfer position and/or during guiding of the energy-transfer unit and the energy-receiving unit into the energy-transfer position and/or during medical treatment.

* * * * *